(12) United States Patent
Devaux et al.

(10) Patent No.: US 10,407,371 B2
(45) Date of Patent: Sep. 10, 2019

(54) METHOD FOR PRODUCING ACROLEIN AND/OR ACRYLIC ACID FROM GLYCEROL

(71) Applicant: Arkema France, Colombes (FR)

(72) Inventors: Jean-Francois Devaux, Soucieu en Jarrest (FR); Michel Fauconet, Valmont (FR); Nabil Tlili, Mulhouse (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 15/354,146

(22) Filed: Nov. 17, 2016

(65) Prior Publication Data

US 2017/0088500 A1 Mar. 30, 2017

Related U.S. Application Data

(62) Division of application No. 14/395,128, filed as application No. PCT/FR2013/050730 on Apr. 3, 2013, now Pat. No. 9,527,791.

(30) Foreign Application Priority Data

Apr. 18, 2012 (FR) ...................................... 12 53557

(51) Int. Cl.
*B01J 19/24* (2006.01)
*B01J 8/06* (2006.01)
*C07C 45/51* (2006.01)
*C07C 45/52* (2006.01)
*C07C 51/235* (2006.01)

(52) U.S. Cl.
CPC ............. *C07C 45/512* (2013.01); *B01J 8/065* (2013.01); *B01J 8/067* (2013.01); *B01J 19/2425* (2013.01); *C07C 45/52* (2013.01); *C07C 51/235* (2013.01); *B01J 2208/00221* (2013.01); *B01J 2208/00557* (2013.01); *B01J 2208/00849* (2013.01); *B01J 2219/00033* (2013.01); *B01J 2219/00036* (2013.01); *B01J 2219/00038* (2013.01); *Y02P 20/584* (2015.11)

(58) Field of Classification Search
CPC . B01J 8/065; B01J 8/06; B01J 19/2425; B01J 19/24
USPC ......................................................... 422/619
See application file for complete search history.

(56) References Cited

U.S. PATENT DOCUMENTS 5,387,720 A 2/1995 Neher et al.
5,814,231 A * 9/1998 Borho .................. B01D 9/0036
210/737

(Continued)

FOREIGN PATENT DOCUMENTS

DE 10 2008 038 273 A1 3/2010
JP 2008 110298 A 5/2008

(Continued)

OTHER PUBLICATIONS

Machine translation of DE10200803273A1—May 4, 2018.*

(Continued)

*Primary Examiner* — Huy Tram Nguyen
(74) *Attorney, Agent, or Firm* — Lynn B. Morreale

(57) ABSTRACT

The invention relates to the production of acrolein and/or acrylic acid from glycerol, and more particularly to a method for continuous production of a stream comprising acrolein by dehydration of glycerol, comprising cycles of reaction and regeneration of a dehydration catalyst.

4 Claims, 7 Drawing Sheets

(56) References Cited

U.S. PATENT DOCUMENTS

| | | |
|---|---|---|
| 8,829,246 B2 | 9/2014 | Dubois |
| 2008/0214384 A1 | 9/2008 | Redlingshofer et al. |
| 2011/0030421 A1* | 2/2011 | Stahl .................... B01D 5/0015 |
| | | 62/532 |
| 2011/0152582 A1 | 6/2011 | Strohm et al. |

FOREIGN PATENT DOCUMENTS

| | | |
|---|---|---|
| JP | 2008 137950 A | 6/2008 |
| WO | WO 2006/087083 A2 | 8/2006 |
| WO | WO 2006/087084 A2 | 8/2006 |
| WO | WO 2008/052993 A2 | 5/2008 |
| WO | WO 2009/044081 A1 | 4/2009 |
| WO | WO 2009/128555 A2 | 10/2009 |
| WO | WO 2010/046227 A1 | 4/2010 |
| WO | WO 2011/033689 A1 | 3/2011 |

OTHER PUBLICATIONS

Tanabe, Kozo, et al; Studies in Surface Science and Catalysis; vol. 51—New Solid Acids and Bases, Their Catalytic Properties. Chapter 2—"Determination of Acidic and Basic Properties on Solid Surfaces" pp. 5-11.

* cited by examiner

METHOD FOR PRODUCING ACROLEIN AND/OR ACRYLIC ACID FROM GLYCEROL

CROSS-REFERENCE TO RELATED APPLICATIONS

This application is a divisional application of U.S. Ser. No. 14/395,128, filed Oct. 17, 2014 which is a national stage application under 35 U.S.C. § 371 of PCT/FR2013/050730, filed Apr. 3, 2013, which claims benefit to French patent application FR 1253557, filed Apr. 18, 2012, Patented; Patent No. FR 2989684 B1 on Oct. 31, 2014.

The work leading to the present invention received financial support from the seventh framework program of the European Community FP7/2007-2013 based on subsidy agreement No. 228867.

FIELD OF THE INVENTION

The present invention relates to the production of acrolein and/or acrylic acid from glycerol, and relates more particularly to a method for continuous production of a stream comprising acrolein by dehydration of glycerol, comprising cycles of reaction and regeneration of the dehydration catalyst.

It also relates to a plant for producing this continuous stream of acrolein efficiently in terms of energy consumption and productivity, without high capital costs and in good conditions of safety.

TECHNOLOGICAL BACKGROUND

Resources of fossil origin, such as petroleum cuts, for the chemical industry will be exhausted some decades from now. That is why, for some years, industrial corporations have oriented their research and development activities toward so-called "biosourced" methods of synthesis using renewable natural raw materials.

Acrolein, an important synthesis intermediate for the chemical industry, is produced industrially by gas-phase oxidation of propylene by the oxygen of the air in the presence of catalytic systems based on mixed oxides. Its manufacture is thus dependent upon raw material of fossil origin.

Acrolein is a key intermediate for the synthesis of methylmercapto-propionaldehyde and methionine, a synthetic protein used as an animal feed supplement, which has been widely adopted as a substitute for fish meal. Acrolein is also used for producing acrylonitrile, glutaraldehyde or pyridine. polymer of acrylic acid or, after esterification with alcohols, for producing a polymer of the corresponding ester. These polymers are used as they are or as copolymers in fields as varied as hygiene (for example in the production of superabsorbents), detergents, paints, varnishes, adhesives, paper, textiles, leather, etc.

Glycerol, obtained from vegetable or animal oils in the production of biodiesel fuels, is one of the raw materials envisaged as a substitute for propylene for producing acrolein, glycerol being submitted to a reaction of catalytic dehydration leading to acrolein. Such a method thus makes it possible to rectify the problem of replacement of propylene, and to respond to the concept of green chemistry in a more general context of protection of the environment.

The reaction of dehydration of glycerol to acrolein has already been the subject of numerous studies, notably in the search for catalytic systems ensuring complete conversion of glycerol, as well as a yield and selectivity for acrolein suitable for production on an industrial scale.

We may mention for example documents U.S. Pat. No. 5,387,720 and WO20061087084, which describe a method of synthesis of acrolein in the presence of solid acid catalysts, characterized by their Hammett acidity; such catalysts may notably be selected from natural or synthetic siliceous materials, acidic zeolites, oxides impregnated with inorganic acids, mono-, di-, tri- or polyacids, oxides or mixed oxides or heteropolyacids.

Other catalytic systems with activity for dehydration of glycerol have been proposed, for example solids based on doped iron phosphate, partially salified heteropolyacids, heteropolyacids supported on porous titanium oxide, or mixed oxides of phosphorus and of vanadium (WO 2009/044081; WO 2009/128555; WO 2011/033689; WO 2010/046227).

However, the reaction of catalytic dehydration of glycerol to acrolein is always accompanied by secondary reactions leading to the formation of byproducts such as hydroxypropanone, propanaldehyde, acetaldehyde, and acetone, but also formation of high-boiling compounds such as phenol, polyaromatic compounds or compounds resulting from the polycondensation of glycerol.

The presence of byproducts requires steps of separation/purification for recovering either purified acrolein, or a stream containing acrolein that can be submitted to a subsequent step of oxidation for producing acrylic acid.

The high-boiling compounds are partly the cause of coke formation on the catalyst.

This leads to deactivation of the catalyst, and consequently a decrease in conversion of glycerol and in selectivity for acrolein.

The catalyst must therefore be changed periodically in order to maintain satisfactory economic efficiency. Catalyst life depends on the operating conditions of the system, and may range from a few hours to a few days. Periodical regeneration of the catalyst compensates the deactivation at least partially, giving satisfactory catalytic activity again, but greatly reduces plant productivity.

Many studies have thus related to improvement of productivity, notably by combining various operating conditions.

Thus, in document WO 2006/087083 in the name of the applicant, it is proposed to use molecular oxygen during the reaction of dehydration of glycerol to acrolein to reduce the formation of coke on the catalyst. In this method for producing acrolein, catalyst regeneration may be performed ex-situ, for example for a fluidized bed, by continuous extraction of spent catalyst and combustion under air, then reloading of fresh catalyst without stopping production. In this case, regeneration is carried out at a temperature and a pressure which are not necessarily the same as those for the reaction. Catalyst regeneration may also be carried out continuously in-situ at the same time as the reaction, taking into account the presence of a small amount of molecular oxygen in the reactor. In this case, regeneration is carried out at the temperature and at the pressure of the reaction, and is more like partial inhibition of deactivation: in fact, the oxygen content is not sufficient for conserving a sufficient activity of the catalyst after some tens of hours to some days.

In the two-step method for producing acrylic acid from glycerol described in document DE 10 2008038273, dehydration of glycerol is carried out in the presence of a catalyst divided into at least two parts, one part being in reaction mode and the other part in regeneration mode. The reaction is carried out at a temperature in the range from 200° C. to 400° C., whereas catalyst regeneration is carried out at a temperature in the range from 300° C. to 600° C., in oxidizing conditions using a gas containing oxygen, in particular a gas mixture comprising less than 10 vol % of oxygen, or in reducing conditions in the presence of a gas containing hydrogen. The two catalyst beds, fixed or fluidized, function alternately in reaction mode and in regeneration mode in two reactors in parallel.

In the method for producing acrolein described in document WO 2008/052993, the problem of regeneration of the dehydration catalyst is solved by employing a circulating bed reactor operating at a temperature between 200° C. and 650° C.; the catalyst, after separation of the reaction stream, is regenerated continuously in the presence of a gas containing oxygen at a temperature in the range from 400° C. to 700° C., with combustion of the coke supplying the heat that is used for the reaction, in particular for vaporizing the reactor feed stream.

Document US 2008/0214384 describes a method for producing acrolein from glycerol in the presence of a tungsten-based acid catalyst comprising at least one promoter selected from a list of elements, the presence of this promoter reducing the tendency for carbonization of the catalyst and facilitating its regeneration. The dehydration reaction is carried out at a temperature between 150° C. and 450° C. For regeneration carried out in the presence of oxygen or hydrogen, a high temperature is used, between 100° C. and 800° C., which does not correspond to the reaction temperature. The method may be implemented using reaction/regeneration cycles in two separate reactors to obtain a continuous stream of acrolein.

In patent application JP 2008-137950, it is proposed to use a dehydration catalyst containing a metal selected from Pt, Pd, Ru, Ir, Cu and Au, making it possible to prolong catalyst life and reduce the temperature and regeneration time, in a method for producing acrolein from glycerol.

In the method described in patent application JP 2008-110298, regeneration of the catalyst for glycerol dehydration is carried out at a temperature above the calcination temperature in order to reduce the regeneration time and return to a level of catalytic activity of the same order as the initial catalytic activity. The temperature of the catalyst during regeneration is controlled on the basis of the regeneration temperature, the concentration of oxidizing agent and the flow of oxidizing agent. A plurality of reactors operating either in reaction or in regeneration makes it possible to avoid interrupting the production of acrolein.

Document US 2011/0152582 describes particular plant configurations for carrying out a reaction of dehydration and for regenerating the phosphorus-based catalyst used. In this plant, feed of the reactive stream is stopped sequentially in order to feed the reactor with an oxidizing gas or a reducing gas for regenerating the catalyst.

Despite these various developments, there is still a need for new methods for further improving the productivity of the reaction of dehydration of glycerol to acrolein, and consequently the productivity of manufacture of acrylic acid from glycerol on an industrial scale.

Now, the inventors discovered that this need could be satisfied by combining cycles of reaction with cycles of regeneration in precise operating conditions, and these cycles can be integrated in a particular reactor configuration for continuous production of a stream containing acrolein.

One aim of the present invention is therefore to supply a method and a device for producing a stream comprising at least acrolein obtained by dehydration of glycerol, which can be fed continuously with glycerol efficiently in terms of energy consumption and productivity, without high capital costs and in good conditions of safety.

SUMMARY OF INVENTION

The present invention thus relates to a method for continuous production of a stream comprising at least acrolein, comprising the following steps:
- a step (a) of reaction of a gaseous reaction stream comprising at least glycerol, on contact with a solid acid catalyst contained in a reactor zone maintained at a temperature in the range from 250° C. to 350° C. to obtain a converted stream comprising at least acrolein,
- a step (b) of regeneration of said solid catalyst with a gaseous stream comprising at least oxygen, characterized in that:
  (i) step (b) is carried out at a regeneration temperature similar to the reaction temperature in step (a), and
  (ii) the hot spot of the catalyst during step (b) does not exceed 100° C. above the temperature of the reactor zone containing the catalyst in regeneration mode, and
  (iii) step (a) and step (b) are applied simultaneously, each on at least one reactor zone in the form of cycles in reaction mode and in regeneration mode offset from one zone to another.

The invention also relates to a method for producing acrylic acid from glycerol, comprising a first step of production of a stream comprising at least acrolein by the method described above and a step of oxidation of acrolein to acrylic acid.

The invention also relates to plant for continuous production of a stream comprising at least acrolein.

The present invention makes it possible to overcome the drawbacks of the prior art. More particularly it supplies a compact plant for production of acrolein, allowing optimal control of the operating conditions leading to a continuous gaseous stream containing acrolein.

The invention is particularly suitable for the reaction of dehydration of glycerol leading to formation of acrolein, for which catalyst deactivation has a characteristic duration with an order of magnitude greater than one hour and less than one month (the deactivation time being defined as the reaction time at the and of which the acrolein yield has dropped by 15% relative to the maximum yield) and for which the deactivation time is between 0.05 times and 20 times the regeneration time (defined as the time at the end of which a catalyst that has undergone deactivation regains its initial efficiency, i.e. makes it possible to regain the same maximum yield as in the preceding cycle and the same deactivation time).

Figure 1:
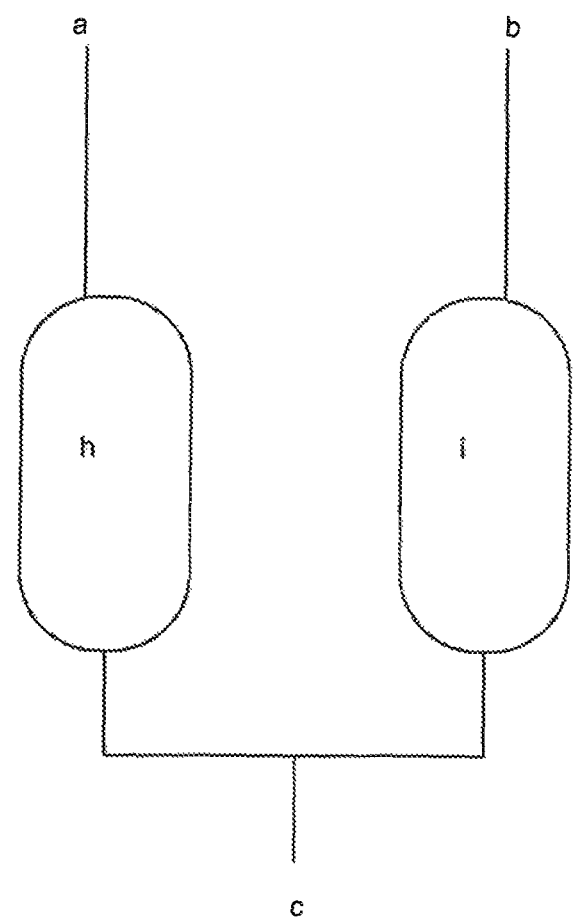
FIGS. 1 and 2 show schematically an embodiment of the invention according to a configuration with 2 reactors in parallel.

Other particular features and advantages of the invention will become clear on reading the detailed description given below.

DETAILED DESCRIPTION

The method of production according to the invention comprises a series of successive cycles, each cycle comprising successively a reaction step (a) and a regeneration step (b), in a reactor comprising at least two zones containing a catalyst, or in at least two reactors containing a catalyst.

According to step (a) of the method according to the invention, a gaseous reaction stream comprising glycerol is brought into contact with an acidic solid able to catalyze the reaction of dehydration of glycerol to acrolein. Aqueous solutions, with a concentration that may range from 20 to 100 wt %, are generally used as the source of glycerol.

Any source of glycerol is conceivable: the glycerol may for example come from processes for hydrolysis or saponification or transesterification of vegetable or animal oils or of recycled oils. The glycerol used may optionally comprise organic impurities in an amount generally below 5%.

Besides glycerol, the gaseous reaction stream may comprise steam, and inert compounds such as CO, $CO_2$ and/or $N_2$, Ar. It may further contain oxygen or a gas containing oxygen as described in applications WO 06/087083 and WO 06/114506. The water/glycerol weight ratio may vary widely, for example between 0.04/1 and 9/1 and preferably between 0.3/1 and 3/1.

The reaction of dehydration of glycerol is carried out in the presence of a solid acid catalyst at an absolute pressure between 1 and 5 bar (100 and 500 kPa). The reactor temperature is between 250° C. and 350° C., preferably between 280° C. and 340° C., in particular between 290° C. and 330° C.

Suitable catalysts are materials used in a gaseous or liquid reaction mixture, in heterogeneous phase, which have a Hammett acidity, denoted H0, less than +2. As pointed out in U.S. Pat. No. 5,387,720, which refers to the article by K. Tanabe et al. in "Studies in Surface Science and Catalysis". Vol. 51, 1989, chap 1 and 2. Hammett acidity is determined by titration with amine using indicators or by gas-phase adsorption of a base.

These catalysts may be selected from natural or synthetic siliceous materials or acidic zeolites; mineral supports, such as oxides, coated with inorganic acids, mono-, di-, tri- or polyacids; oxides or mixed oxides or else heteropolyacids or salts of heteropolyacids. It will be possible to use a combination of the aforementioned species.

These catalysts may consist of a salt of heteropolyacid in which protons of said heteropolyacid are exchanged with at least one cation selected from the elements belonging to Groups I to XVI of the periodic table, these salts of heteropolyacid containing at least one element selected from the group comprising W, Mo and V.

Among the mixed oxides, we may mention in particular those based on iron and phosphorus and those based on cesium, phosphorus and tungsten.

The catalysts are notably selected from zeolites, sulfonic acid-based composites of fluorinated polymers (Nafion®), chlorinated aluminas, acids and salts of phosphotungstic acid or silicotungstic acid, and various solids of the metal oxide type such as tantalum oxide $Ta_2O_5$, niobium oxide $Nb_2O_5$, alumina $Al_2O_3$, titanium dioxide $TiO_2$, zirconia $Zr_2$, tin oxide $SnO_2$, silica $SiO_2$ or aluminosilicate $SiO_2$—$Al_2O_3$, impregnated with acid functions such as borate $BO_3$, sulfate $SO_4$, tungstate $WO_3$, phosphate $PO_4$, silicate $SiO_2$, or molybdate $MoO_3$, or a mixture of these compounds.

The aforementioned catalysts may further comprise a promoter such as Au, Ag, Cu, Pt, Rh, Pd, Ru, Sm, Ce, Yt, Sc, La, Zn, Mg, Fe, Co, Ni, or montmorillonite.

The preferred catalysts are the acidic solids comprising tungsten such as tungsten oxide or the tungstic heteropolyacids such as silicotungstic acid or phosphotungstic acid or salts thereof supported on silica, alumina, zirconia or titanium oxide supports.

Step (b) of the method according to the invention consists of regenerating the dehydration catalyst by means of a regeneration stream, preferably containing an oxidizing substance such as oxygen allowing combustion of the coke that is the cause of catalyst deactivation. This regeneration stream may be purely gaseous or may comprise a liquid component, and is preferably purely gaseous. It comprises oxygen, and may optionally comprise one or more inert heat-transfer compounds such as CO, $CO_2$ and/or $N_2$. For example, the regeneration stream is air.

Advantageously, the gaseous regeneration stream may further contain water as heat-transfer fluid, which generates a gas mixture containing water and oxides of carbon after regeneration, and this mixture may be recycled to the reaction for diluting the reaction stream of glycerol.

The regeneration step begins when feed of glycerol onto the catalyst is stopped.

Catalyst regeneration is carried out at a temperature similar to the reaction temperature in step (a) and, correlatively, the reaction step is carried out at a temperature similar to the regeneration temperature in step (b) of the preceding cycle.

In particular, in the case of reactors or reactor zones thermostatically controlled with the aid of a heat-transfer fluid, the reactions are carried out with control of the temperature of the heat-transfer fluid. According to the invention, performing regeneration at a temperature similar to the reaction temperature in step (a) signifies that the temperature of the heat-transfer fluid in the reactor zone during step (b) is at a temperature similar to the temperature of the heat-transfer fluid in step (a).

For simplicity, in the rest of the description "catalyst zone" means a reactor zone containing a catalyst.

"Similar" temperature signifies equal to within plus or minus 20° C., preferably to within plus or minus 10° C., more particularly to within plus or minus 5° C.

This procedure avoids having to change the thermal level of the reactor or of the reactor zones in every reaction/regeneration cycle. In fact, changing the thermal level in every reaction/regeneration cycle would be costly in time and energy and would require appropriate installations.

Surprisingly, the applicant found that these temperature conditions are sufficient to completely restore catalyst activity during the next reaction step.

Combustion of coke is an exothermic reaction; as a result, there is an increase in catalyst temperature during the regeneration step, generally called hot spot. The temperature of the catalyst or of a portion of the catalyst is than above that of the reactor or reactor zone that contains the catalyst. In particular, in the case of reactors thermostatically controlled with the aid of a heat-transfer fluid, the temperature of the catalyst or of a portion of the catalyst is then above that of the heat-transfer fluid. A hot spot in the catalyst at a raised temperature above 450° C. or 500° C. is likely to lead to thermal runaway, but also to premature aging of the catalyst. This also requires having specially adapted reactor metallurgy.

According to the method of the invention, the hot spot is controlled and it is maintained at max. 100° C., preferably at 50° C., in particular at max. 20° C., above the temperature of the reactor or reactor zone that contains the catalyst in regeneration mode. In particular, in the case of reactors or reactor zones comprising a heat-transfer fluid, the temperature of the hot spot is maintained at max. 100° C., preferably at 50° C., in particular at max. 20° C., above that of the heat-transfer fluid.

For this purpose, the oxygen content in the regeneration stream is advantageously below 10 vol %, preferably below 8 vol %. Alternatively, an oxygen content that increases over the course of regeneration is used: in the first part of regeneration, which lasts between 5 and 100% and preferably between 10 and 40% of the total regeneration time, the oxygen content is below 10 vol %, and preferably below 8 vol %. After this first part of regeneration, when a proportion of the coke has been consumed, it will be possible if necessary to increase the oxygen concentration continually or in stages until an oxygen concentration from about 9 to 22 vol %, or even more, is reached.

Moreover, removal of the calories generated may be promoted by using a multiple-tube reactor with tubes of small section (generally less than 15 cm$^2$ and preferably less than 5 cm$^2$) brought into contact with a heat-transfer fluid or a plate-type reactor or a fluidized bed reactor comprising heat exchangers. In this case, the space velocity in regeneration mode (flow rate in normal liters per hour of gas sent to the reactor divided by the apparent volume of catalyst expressed in liters) may vary over a wide range from 50 to 10000 h$^{-1}$ and preferably between 200 and 2000 h$^{-1}$.

Alternatively, the catalyst zone is supplied with the regeneration stream at a high space velocity (generally above 400 h$^{-1}$ and preferably above 700 h$^{-1}$ and preferably above 1500 h$^{-1}$), which can thus carry away the calories generated.

Generally the heat generated in an exothermic reaction, such as regeneration, is recovered, for example in the form of steam. The method according to the invention makes it possible to smooth the production of heat over time, avoiding having a strong exothermic effect followed by a very slight exothermic effect, as in this case we would have overproduction of steam during one period and then underproduction during the next period, which would not be satisfactory economically.

It is advantageous to have two or more catalyst zones in parallel, so that step (a) and step (b) can be applied at the same time on at least one catalyst zone. One and the same catalyst zone operates according to a reaction/regeneration cycle that is repeated many times and the cycles of reaction/regeneration are offset from one zone to another, For a given catalyst zone, the cycle consists of starting step (a) by sending a gaseous reaction stream containing glycerol. The acrolein yield increases (phase of catalyst activation) and then reaches a maximum and decreases slowly (catalyst deactivation associated with coking). Step (a) ends when the acrolein yield has fallen relative to the maximum yield by a value fixed by the technical conditions (so as to have a flow that is as constant as possible) and economic conditions of the process, generally from 1 to 30%. The duration of step (a) depends on the nature of the catalyst used and the amount of this catalyst and the reaction conditions (especially the amount of oxygen used and the temperature). According to the invention, this duration varies from 1 hour to 1 month.

The duration of step (b) depends on the nature of the catalyst, the space velocity, the temperature and the oxygen concentration. This duration is adjusted so that the catalyst regains its efficiency in step (a) of the next cycle. According to the invention, this duration varies between 0.05 and 20 times the duration of step (a) and between 3 minutes and 7 days.

According to a particular embodiment of the invention, an increasing temperature gradient may be applied to the reactor, or if applicable to the heat-transfer fluid providing thermostatic control of the reactor, for the entire duration of step (a), between 1 and 30° C. between the start and end of step (a). Preferably, after a constant initial temperature for 0 to 50% of the duration of step (a), a continuous increase will be applied in the second part of step (a). It will also be possible to raise the temperature in stages of equal temperature difference from 0.1 to 10° C. and of equal duration.

In the same way, an increasing temperature gradient may be applied to the reactor or reactor zone, or if applicable to the heat-transfer fluid providing thermostatic control of the reactor or reactor zone, for the entire duration of step (b) between 1 and 30° C. between the start and end of step (b). Preferably, after a constant initial temperature for 0 to 50% of the duration of step (b), a continuous increase will be applied in the second part of step (b). It will also be possible to raise the temperature in stages of equal temperature difference from 0.1 to 10° C. and of equal duration. At the end of step (b), generally the temperature of the reactor or reactor zone will be brought back to the temperature of step (a).

The reaction/regeneration cycle is applied in one and the same zone for as long as regeneration makes it possible to restore catalyst efficiency. Generally one and the same catalyst charge can be used for more than 4 months and preferably for more than 1 year.

Advantageously, the number of catalyst zones will be adjusted depending on the ratio of the duration of step (a) to the duration of step (b), in order to optimize the size of the reactors required: the ratio of the number of zones in reaction to the number of zones in regeneration will be equal to or slightly below the ratio of the durations of steps (a) and (b). For example, if the duration of step (a) is equal to 20 hours and the duration of step (b) is equal to 9 hours, it will be possible to choose to have 3 catalyst zones, with 2 zones operating in reaction mode while one zone operates in regeneration mode. Alternatively, it will be possible to have 6 catalyst zones, with 4 zones operating in reaction mode and 2 zones operating in regeneration mode.

According to a first embodiment of the invention, steps (a) and (b) are carried out on two or more catalyst zones placed in at least two reactors in parallel, each reactor being supplied separately. In the configuration with 2 reactors, shown in FIGS. 1 and 2, each reactor (h) and (i) comprises a single catalyst zone, which may be fixed-bed or fluidized-bed.

In the configuration shown in FIG. 1, during the first part of the cycle, the gaseous reaction stream is sent into "a" and the regeneration stream is sent into "b". In the second part of the cycle, the gaseous reaction stream is sent into "b" whereas the regeneration stream is sent into "a".

Figure 2:
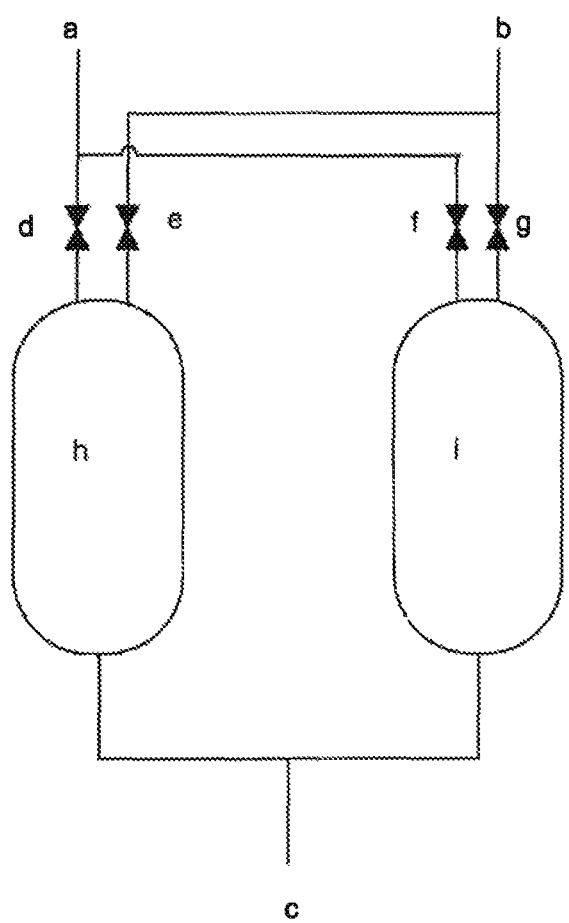

In the configuration shown in FIG. 2, during a first part of the cycle, the gaseous reaction stream "a" is sent into reactor (h) via valve (d), valve (f) being closed. Reactor (h) is in reaction mode. The regeneration stream "b" is sent into reactor (i) via valve (g) which is open, valve (e) being closed. In a second part of the cycle, valves (d) and (g) are closed and valves (e) and (f) are open. Reactor (h) is then in regeneration mode and reactor (i) is then in reaction mode. All the gaseous streams leaving the two reactors are combined to form stream "c".

According to a second embodiment of the invention, steps (a) and (b) are carried out in one and the same reactor comprising at least 2 catalyst zones, each zone being supplied separately. This configuration is shown in FIGS. 3 to 5, where several catalyst zones are situated spatially in one and the same reactor comprising as many separate feeds as reaction zones.

The characteristic feature of the reactor is separation of the gaseous streams in each of the catalyst zones, as well as in the feed zone and/or in the withdrawal zone. This separation may be effected for example with a partition between the catalyst zones and/or in the feed zones and/or in the withdrawal zones.

Figure 3:
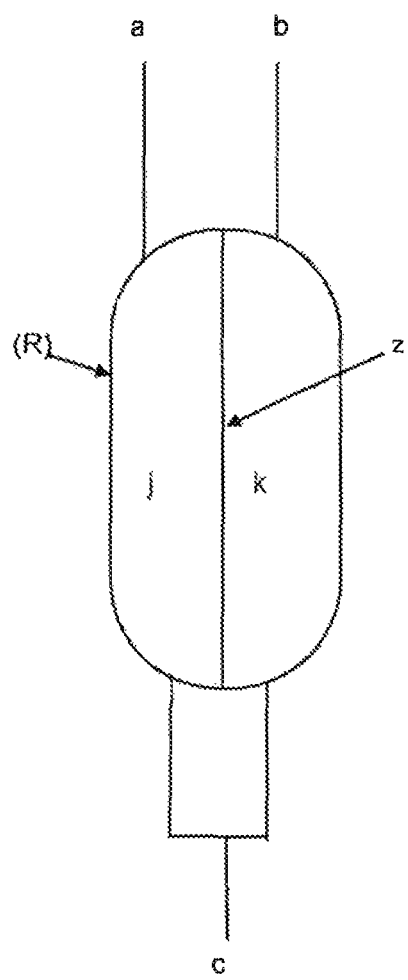
FIGS. 3 and 4 show schematically an embodiment of the invention according to a configuration with a single reactor comprising 2 zones, one operating in reaction mode and the other in regeneration mode.

In the configuration shown in FIG. 3, reactor (R) contains 2 catalyst zones (j) and (k) separated by a partition (z). In a first part of the cycle, the gaseous reaction stream is sent at "a" into catalyst zone (j). The regeneration stream is sent at "b" into zone (k). Zone (j) is then in regeneration mode and zone (k) is then in reaction mode. All the gaseous streams leaving the two reactors are combined to form stream "c".

Figure 4:
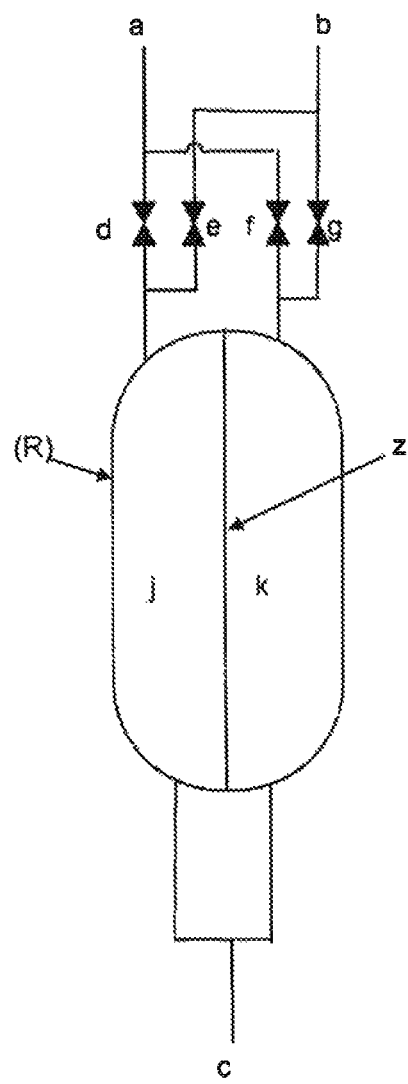
Figure 5:
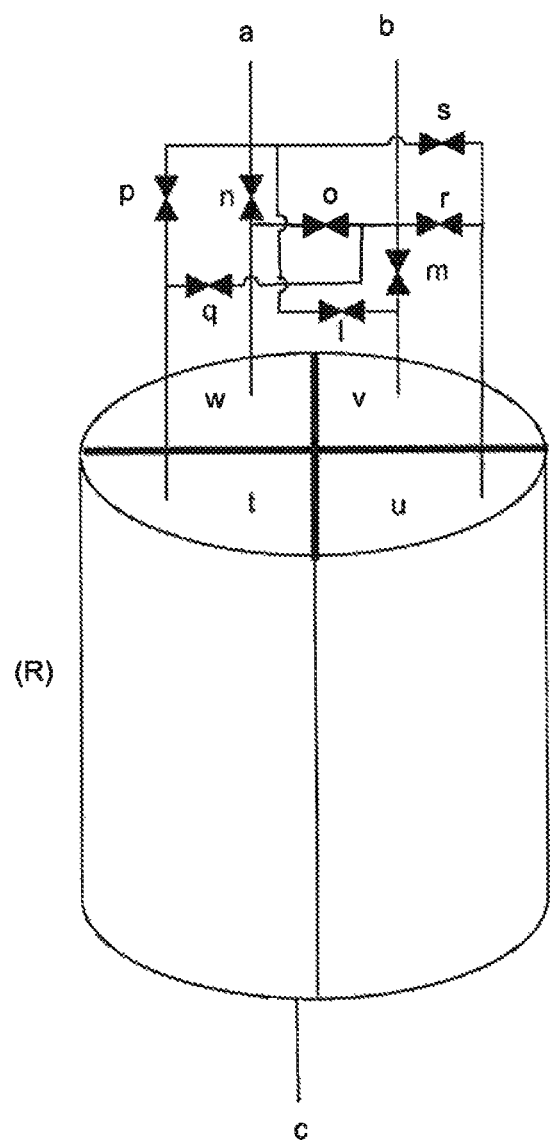
FIG. 5 shows schematically an embodiment of the invention according to a configuration with a single reactor comprising 4 zones alternately in reaction mode and in regeneration mode.

In the configuration shown in FIG. 4, reactor (R) contains 2 catalyst zones (j) and (k) separated by a partition (z). In a first part of the cycle, the gaseous reaction stream "a" is sent into catalyst zone (j) by adjusting the position of valves (d) and (f). This zone (j) is in reaction mode. The regeneration stream "b" is sent into zone (k) by adjusting the position of valves (g) and (e). In a second part of the cycle, the positions of valves (d), (e), (f) and (g) are reversed: zone (j) is then in regeneration mode and zone (k) is than in reaction mode. All the gaseous streams leaving the two reactors are combined to form stream "c".

In the reactor shown schematically in FIG. 5, four catalyst zones (t), (u), (v) and (w) may be supplied selectively with the gaseous reaction stream "a" or the regeneration stream "b" with a set of valves. Withdrawal from the 4 catalyst zones is common and forms stream "c".

In the reactors in FIGS. 3 to 5, the number of catalyst zones operating in reaction mode may be equal to the number of zones operating in regeneration mode. In this case, 50% of the catalyst is in acrolein production mode.

Alternatively, the number of catalyst zones operating in reaction mode may be greater than the number of zones operating in regeneration mode. For example, in the case of the reactor comprising four catalyst zones shown schematically in FIG. 5, it is possible to operate three zones in reaction mode with time offset, and one zone in regeneration mode, which limits the proportion of catalyst in regeneration to 25% and makes it possible to fix an average production of acrolein at outlet.

In the reactor in FIG. 5, in a first part of the cycle, zones (t), (u), (v) are in reaction and zone (w) is in regeneration, line "a" is supplied with a gaseous reaction mixture, whereas line "b" is supplied with a gaseous regeneration mixture by setting valves (p), (s), (l) and (o) in the open position and valves (q), (r), (m) and (n) in the closed position. In a second part of the cycle, zones (u), (v) and (w) are in reaction and zone (t) in regeneration by setting valves (p) and (o) to the closed position and by opening valves (q) and (n). Then in a third part of the cycle, zone (u) is in regeneration and the other zones are in reaction owing to adjustment of the appropriate valves. In a fourth part of the cycle, zone (v) is in regeneration and the other zones are in reaction owing to adjustment of the appropriate valves. Then the cycle is begun again from the start.

In these various configurations, the gaseous stream of acrolein obtained from the reaction and the gaseous stream from regeneration are not necessarily mixed at the outlet, i.e. each of the zones may have a separate gaseous stream outlet.

Optionally, the gaseous stream of acrolein may be cooled to below 250° C. and preferably to below 230° C. by an exchanger positioned in the reactor after the catalyst bed (or in an exchanger just after the reactor outlet), to avoid reaction of the acrolein.

Optionally, it is possible to operate in regeneration mode by recycling some or all of the gaseous stream leaving the catalyst zone to the entrance of the zone, passing through a fan and a heat exchanger, so that the heat generated by regeneration is removed from the reactor by the regeneration gases, which circulate at high space velocity over the catalyst.

Optionally, the gaseous stream leaving a zone that is operating in regeneration may either be recycled to the inlet of a zone that is operating in reaction for diluting the gaseous reaction stream of glycerol, or may be directed to a thermal oxidizer for removal. Alternatively, a part of the stream leaving the zone operating in regeneration mode is recycled to the inlet of a zone that is operating in reaction, the rest being directed to a thermal oxidizer.

In these various configurations, the gaseous stream leaving a zone that is operating in regeneration may also be mixed with the gaseous stream of acrolein leaving a zone that is operating in reaction. In a particular configuration, illustrated for example in FIGS. 1 to 5, all the gaseous streams are mixed at the outlet. This offers the advantage of not requiring treatment of the gaseous stream from regeneration, but results in production of a stream of acrolein diluted in the inert compounds ($CO$, $CO_2$, $H_2O$). This stream of acrolein is then submitted to various treatments in the steps that follow those of the method of the invention.

The method according to the invention may be implemented in a fixed bed or in a fluidized bed, preferably in a fixed bed.

The invention also relates to the production of acrylic acid from glycerol, comprising a first step of production of a stream comprising at least acrolein by the method described above and a step of oxidation of acrolein to acrylic acid.

Of course, this method for producing acrylic acid may comprise other preliminary, intermediate or subsequent steps, provided they allow a grade of acrylic acid to be produced.

Thus, notably an intermediate step may be provided between the method for producing the stream containing acrolein and the acrolein oxidation step. This intermediate step may be for example that described in patent application WO 08/087315 in the applicant's name, which makes it possible to remove a proportion of the water contained in the stream of acrolein, so as to adjust this gas to a composition roughly identical to that of the ex-propylene process, for supplying the second step of oxidation of acrolein to acrylic acid. Roughly identical composition means in particular similar concentrations of acrolein, water, oxygen and byproducts. This intermediate step consists of a partial condensation of the water and makes it possible to avoid degradation of the 2nd-stage catalyst of oxidation of acrolein to acrylic acid. Moreover, it makes it possible to remove a proportion of the "heavy" impurities formed at the same time as acrolein.

The invention also relates to plant for continuous production of a stream comprising at least acrolein, said installation comprising:
 a unit for converting glycerol to acrolein
 a source of gaseous reaction stream comprising at least glycerol a source of regeneration stream comprising at least oxygen characterized in that the converting unit comprises:

a reactor R comprising at least two zones containing catalyst, each of the zones being used alternately as reaction zone and as regeneration zone, each of the zones having fluidic connection by a feeding device to source "a" of reaction stream and to source "b" of regeneration stream, a suitable system for each feeding device allowing sequential alternation of supply with reaction stream or with regeneration stream, at least one device for withdrawal of a gas mixture "c" with fluidic connection to the reactor, the reactor zones are controlled thermostatically with a single system of the heat-transfer fluid.

"Fluidic connection" means that there is connection by a system of pipelines able to transport a stream of matter. This connection system may comprise valves, intermediate storage devices, branch connections, heat exchangers, compressors, but not chemical reactors.

Each of the zones comprises one and the same glycerol dehydration catalyst, preferably in the form of a fixed bed. Preferably each of the zones contains an identical amount of catalyst and has identical heat exchange capacity, the zones being thermostatically controlled in the same way. Thus, preferably, the catalyst zones are identical.

According to particular embodiments, the converting unit may comprise a single device for withdrawing gas mixture, or each of the reactor zones has fluidic connection to a device for withdrawing gas mixture.

The plant may comprise one or more of the following features:

The converting unit comprises recycling means positioned between the outlet and the inlet of each of the zones to allow recycling of a stream leaving a zone operating in regeneration mode, either to the inlet of a zone operating in reaction mode, or to the inlet of said zone operating in regeneration mode.

The converting unit comprises heat exchangers for cooling the gaseous streams of acrolein, and/or removing the calories generated by regeneration.

Figure 6:
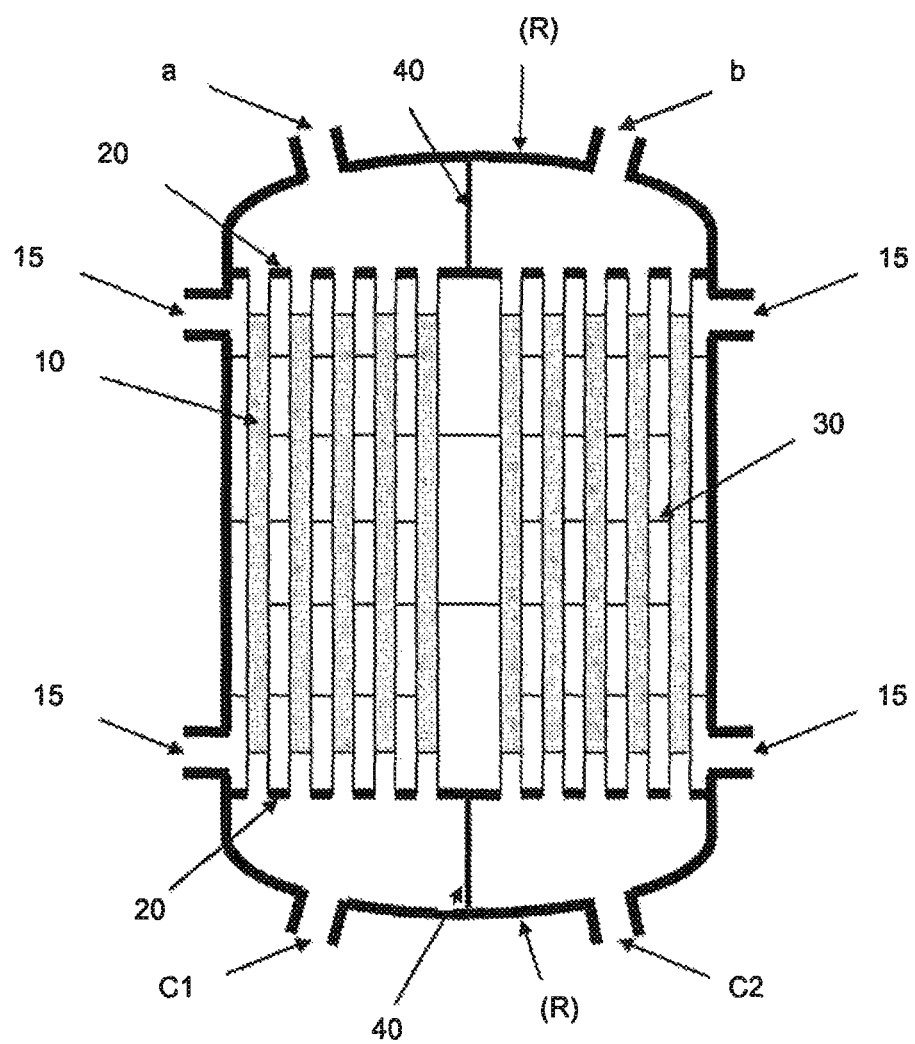
FIGS. 6 and 7 show schematically an embodiment with a multiple-tube reactor comprising 2 reaction zones.
Figure 7:
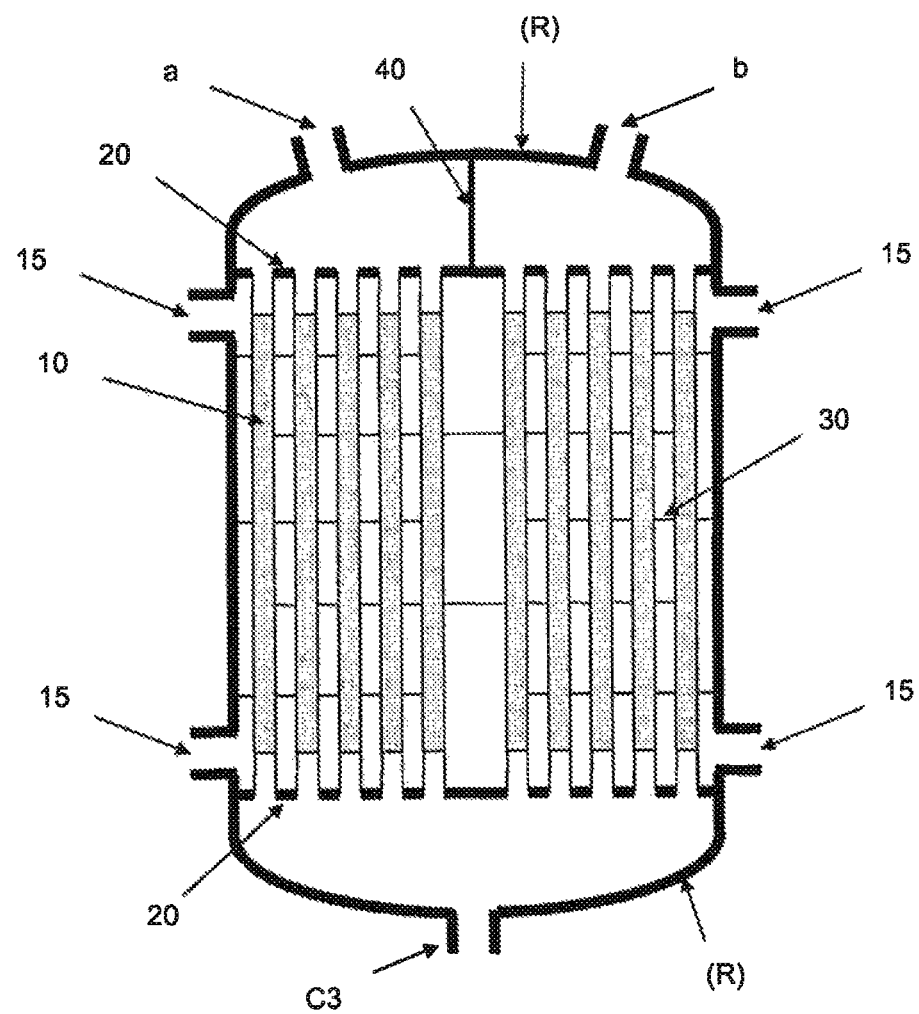

According to a preferred embodiment of the invention, the converting unit comprises a multiple-tube reactor comprising at least two catalyst zones, shown schematically for example in FIGS. 6 and 7 in the particular case of two catalyst zones.

The multiple-tube reactor (R) comprises a large number of tubes (10) that contain the catalyst and are fixed by tube plates (20). Heat-transfer fluid is supplied and withdrawn via openings (15) and its circulation between the tubes (10) is guided by plates (30) arranged perpendicularly to the tubes (10) to allow better heat exchange. A single circuit of heat-transfer fluid provides thermostatic control of all of the catalyst zones. The characteristic feature of the reactor according to the invention is separation of the catalyst zones, which is provided by the installation of plates (40) positioned between the domes of the reactor (R) and the tube plates (20). Supply of the gaseous reaction stream "a" and regeneration stream "b" and withdrawal c1 and c2 are provided by different openings.

The reactor shown schematically in FIG. 6 may be used in several ways. In a first manner of use, supply of the gaseous reaction stream "a" and of the gaseous regeneration stream "b" is provided alternately via openings (a) and (b) and the gases leaving the reaction zone and regeneration zone are withdrawn via openings (c1) and (c2). In a second manner of use, the gaseous reaction stream is supplied via opening (c1) for part of the time and via opening (c2) for the rest of the time, and supply of the gaseous regeneration stream and withdrawal of the reaction gases are provided respectively via openings (b) and (a) for part of the time and via openings (a) and (b) for the rest of the time.

The reactor shown schematically in FIG. 7 only comprises a single separating plate (40) and a single opening (c3). In a first embodiment, the gaseous reaction stream and the gaseous regeneration stream are supplied alternately via openings (a) and (b) and the gases leaving the reaction zone and those leaving the regeneration zone are mixed and leave via opening (c3). In a second embodiment, the gaseous reaction stream is supplied via opening (c3) and the gaseous regeneration stream is supplied and the reaction gases are discharged alternately via opening (a) and via opening (b). In the latter case, the gaseous stream leaving regeneration is mixed with the reaction gas coming in onto the catalyst and containing glycerol. This reactor may be used with the opening (c3) positioned at the top of the reactor, or with the opening positioned at the bottom as in FIG. 7.

In the case of a multiple-tube reactor comprising more that 2 reaction zones, it is necessary to adapt the number of separating plates and the number of openings for supply and withdrawal in the domes of the reactors.

The invention will be better understood from the following examples, which are nonlimiting and purely illustrative.

Experimental Section

Example 1

According to the Invention

A 316-liter stainless-steel reaction tube with diameter of 29 mm and height of 1 m, immersed in a salt bath (eutectic mixture $KNO_3$, $NaNO_3$, $NaNO_2$) provided with resistance heating, is charged with 0.39 liters of $HPW/TiO_2$ catalyst, prepared according to example 3 of patent application WO 2011/33689. A positive-displacement pump and 2 mass flow regulators make it possible to send, respectively, a glycerol/water mixture, nitrogen and air to an electrically-heated vaporizer connected to the reactor. Downstream of the reactor, an automatic valve controlled by a pressure sensor allows the desired pressure to be maintained in the reactor. The gaseous stream leaving this valve may be sent for analysis purposes to a column for extraction with water. The liquid effluent thus collected at the bottom of the column over the space of several minutes may be weighed and analyzed by gas chromatography.

The salt bath is maintained at 290° C. and the pressure at 1.7 bar relative throughout the experiment.

At time point t=0 and up to t=24 h, a reaction phase is carried out by sending a continuous stream of 780 Nl/h (normal liters per hour) of a glycerol/water/$N_2$/$O_2$ mixture with proportions by volume of 4.7/24.0/69.1/2.2 at 240° C. to the inlet of the reactor. The hot spot of the reactor rises to 334° C. after a few minutes and then decreases, and stabilizes at 305-310° C.

At t=24 h, the regeneration phase is started. From time point t=24 h to t=24 h15, a stream of 743 Nl/h of a water/$N_2$/$O_2$ mixture 25.2/72.5/2.3 is supplied. From t=24 h15 to t=48 h, a stream of 780 Nl/h of a water/$N_2$/$O_2$ mixture 24.0/69.0/7.0 is supplied. During this period, the maximum hot spot is 316° C.

A second cycle of reaction/regeneration is repeated in the same conditions from t=48 h to t=96 h, then a third cycle of reaction/regeneration from t=96 h to t=144 h.

Analysis of the liquid effluent from the column for absorption of the gaseous stream leaving the reactor made it possible to determine the degree of conversion of glycerol and the acrolein yield, from the following formulas:

Conversion of glycerol (%)=100−number of remaining moles of glycerol/number of moles of glycerol introduced.

Acrolein yield (%)=number of moles of acrolein produced/number of moles of glycerol introduced.

The results are presented in Table 1.

TABLE 1

|  | Time (h) | Temperature of the reactor (salt bath) | Maximum hot spot | Glycerol conversion, % | Acrolein yield, % |
| --- | --- | --- | --- | --- | --- |
| Reaction Cycle 1 | 1 h | 290° C. | 334° C. | >99 | 69 |
|  | 5 h |  |  | >99 | 76 |
|  | 23 h |  |  | 97 | 71 |
| Regeneration Cycle 1 | 24-48 h | 290° C. | 316° C. | — | — |
| Reaction Cycle 2 | 49 h | 290° C. | 346° C. | >99 | 70 |
|  | 53 h |  |  | >99 | 73 |
|  | 71 h |  |  | 98 | 65 |
| Regeneration Cycle 2 | 72-96 h | 290° C. | 316° C. | — | — |
| Reaction Cycle 3 | 97 h | 290° C. | 345° C. | >99 | 69 |
|  | 101 h |  |  | >99 | 74 |
|  | 119 h |  |  | 97 | 65 |
| Regeneration Cycle 3 | 120-144 h | 290° C. | 316° C. | — | — |

According to the invention, the acrolein yield is still above 65% after 3 cycles of reaction/regeneration of 48 hours.

Example 2

Comparative

The conditions of example 1 are reproduced between 0 and 24 h and between 24 h and 24 h15.

At t=24 h15, a stream of 780 Nl/h of a water/$N_2$/$O_2$ mixture with proportions by volume 24.0/66.0/10.0 is supplied. Very soon the hot spot exceeds 550° C. and there is thermal runaway.

Example 3

The conditions of example 1 are reproduced, setting the reactor temperature at 290° C. at t=0 and increasing it by 0.5° C. per hour until t=24 h. The acrolein yield is 69% at t=1 h, 75% at t=5 h and 72% at t=23 h.

Example 4

The equipment of example 1 is used, with a reaction tube with 22 mm inside diameter. The conditions of example 1 are reproduced from t=0 to t=24 h, setting the reactor temperature at 300° C.

At t=24 h, the regeneration phase is started. The temperature is increased from 300° C. to 315° C. in the space of 2 hours and then this temperature is maintained until t=46 h and is then lowered to 300° C. in the space of 2 hours. From time point t=24 h to t=34 h, a stream of 156 Nl/h of a water/$N_2$/$O_2$ mixture with proportions by volume 25.0/73.0/2.0 is supplied. From t=34 h to t=48 h, a stream of 270 Nl/h of a water/$N_2$/$O_2$ mixture with proportions by volume 22.0/63.0/15.0 is supplied. During this period, the maximum hot spot is 363° C.

The cycle of reaction/regeneration is reproduced two more times.

The acrolein yield at the end of the first reaction period (t=23 h) is 70%. At the end of the second reaction period (t=71 h) it is 70%, and at the end of the third period (t=119 h) it is 71%.

Example 5

The equipment of example 1 is used, with tungstic zirconia as catalyst (10% $WO_3$ 90% $ZrO_2$) from Daiichi Kigenso (supplier reference Z1044). The conditions of example 1 are reproduced from t=0 to t=24 h but setting the temperature of the salt bath at 300° C.

At t=24 h, the regeneration phase is started. The temperature of the salt bath is increased from 300° C. to 320° C. in the space of 3 hours and then this temperature is maintained until t=46 h and then is lowered to 300° C. in the space of 2 hours. From time point t=24 h to t=34 h, a stream of 156 Nl/h of a water/$N_2$/$O_2$ mixture with proportions by volume 25/72/3 is supplied. From t=34 h to t=48 h, a stream of 270 Nl/h of a water/$N_2$/$O_2$ mixture with proportions by volume 22/68/10 is supplied. During this period, the maximum hot spot is 353° C.

The reaction/regeneration cycle is reproduced once more in the same conditions.

The average yield of acrolein in the first reaction period (from 0 to 24 hours) is 69%. In the second reaction period (from 48 to 72 hours) it is also 69%.

The invention claimed is:

1. An installation for continuous production of a stream comprising acrolein, said installation comprising:
a unit for converting glycerol to acrolein,
a source of gaseous reaction stream comprising at least glycerol,
a source of gaseous regeneration stream comprising at least oxygen for regeneration of solid acid catalyst,
wherein the converting unit comprises:
a reactor R comprising at least two separated zones each containing said solid acid catalyst, each of the zones being configured to be used simultaneously and alternately as reaction zone and as regeneration zone in cyclical fashion and with reaction mode and regeneration mode being offset from one zone to another, each of the zones having fluid connection by a feeding device to the source "a" of reaction stream and to the source "b" of regeneration stream, wherein the gaseous streams in each of the catalyst zones are separated,
a system adapted to each feeding device allowing sequential alternation of supply with the gaseous reaction stream or with the gaseous regeneration stream,
at least one device for withdrawing a gas mixture c1, c2, c3, with fluidic connection to the reactor,
the reactor zones being controlled thermostatically with a single system of heat-transfer fluid.

2. The installation as claimed in claim 1 comprising a single device for withdrawing gas mixture.

3. The installation as claimed in claim 2, wherein each of the reactor zones has fluidic connection to a device for withdrawing gas mixture.

4. The installation as claimed in claim 1, wherein the reactor R is a multiple-tube reactor comprising tubes (10)

fixed by tube plates (20) and comprising at least one plate (40) positioned between the reactor dome and the tube plates (20).

\* \* \* \* \*